US012625427B2

(12) United States Patent
Oh et al.

(10) Patent No.: US 12,625,427 B2
(45) Date of Patent: May 12, 2026

(54) NAPHTHALIMIDE SULFONATE DERIVATIVE, AND PHOTOACID GENERATOR AND PHOTORESIST COMPOSITION EACH COMPRISING SAME

(71) Applicant: SAMYANG CORPORATION, Seoul (KR)

(72) Inventors: Chun Rim Oh, Seoul (KR); Dae Hyuk Choi, Seoul (KR); Yu Na Choi, Daejeon (KR); Deuk Rak Lee, Daejeon (KR); Ji Eun Choi, Seongnam-si (KR); Ki Tae Kang, Gimpo-si (KR); Min Jung Kim, Sejong (KR); Won Jung Lee, Daejeon (KR); Chi Wan Lee, Daejeon (KR)

(73) Assignee: SAMYANG CORPORATION, Seoul (KR)

( * ) Notice: Subject to any disclaimer, the term of this patent is extended or adjusted under 35 U.S.C. 154(b) by 518 days.

(21) Appl. No.: 18/269,780

(22) PCT Filed: Dec. 28, 2021

(86) PCT No.: PCT/KR2021/020077
§ 371 (c)(1),
(2) Date: Jun. 27, 2023

(87) PCT Pub. No.: WO2022/145986
PCT Pub. Date: Jul. 7, 2022

(65) Prior Publication Data

US 2024/0085786 A1 Mar. 14, 2024

(30) Foreign Application Priority Data

Dec. 28, 2020 (KR) ........................ 10-2020-0185293

(51) Int. Cl.

| | |
|---|---|
| ***G03F 7/039*** | (2006.01) |
| ***C07D 221/14*** | (2006.01) |
| ***G03F 7/004*** | (2006.01) |
| ***G03F 7/26*** | (2006.01) |

(52) U.S. Cl.
CPC ......... *G03F 7/0045* (2013.01); *C07D 221/14* (2013.01); *G03F 7/0392* (2013.01); *G03F 7/0397* (2013.01); *G03F 7/26* (2013.01)

(58) Field of Classification Search
CPC .... G03F 7/0045; G03F 7/0392; G03F 7/0397; G03F 7/32; C07D 221/14
See application file for complete search history.

(56) References Cited

U.S. PATENT DOCUMENTS

| | | | | |
|---|---|---|---|---|
| 2007/0189987 | A1* | 8/2007 | Luukas .................. | A61K 8/732 424/59 |
| 2008/0226581 | A1* | 9/2008 | Luukas ................ | A61K 8/8152 424/78.03 |
| 2012/0289697 | A1 | 11/2012 | Murai et al. | |
| 2016/0085148 | A1 | 3/2016 | Zhang et al. | |
| 2016/0368879 | A1* | 12/2016 | Ikeda .................... | C08L 101/00 |
| 2018/0079724 | A1* | 3/2018 | Yanagisawa ......... | C07D 221/14 |
| 2020/0142307 | A1 | 5/2020 | Momozawa et al. | |

FOREIGN PATENT DOCUMENTS

| | | | |
|---|---|---|---|
| EP | 3 412 745 | A1 | 12/2018 |
| KR | 10-2012-0114353 | A | 10/2012 |
| KR | 10-2017-0125980 | A | 11/2017 |
| KR | 10-2018-0073002 | A | 7/2018 |
| KR | 10-2019-0083378 | A | 7/2019 |
| KR | 10-2020-0052839 | A | 5/2020 |

OTHER PUBLICATIONS

International Search Report for PCT/KR2021/020077 (PCT/ISA/210) mailed on Apr. 5, 2022.

* cited by examiner

*Primary Examiner* — John S. Chu
(74) *Attorney, Agent, or Firm* — Birch, Stewart, Kolasch & Birch, LLP

(57) ABSTRACT

The present invention relates to a naphthalimide sulfonate derivative, and a photoacid generator and a photoresist composition each comprising same and, more specifically, to a naphthalimide sulfonate derivative compound, and a photoacid generator and a photoresist composition each comprising same, wherein the compound has excellent absorbance for light of i-line (365 nm) wavelength, is greatly easy to prepare into a polymerizable composition due to very high solubility in an organic solvent, has good thermal stability, and shows a favorable acid generation rate.

11 Claims, No Drawings

NAPHTHALIMIDE SULFONATE DERIVATIVE, AND PHOTOACID GENERATOR AND PHOTORESIST COMPOSITION EACH COMPRISING SAME

TECHNICAL FIELD

The present invention relates to a sulfonic acid derivative of naphthalimide, and a photoacid generator and a photoresist composition comprising the same, and more specifically, it relates to a sulfonic acid derivative of naphthalimide which has an excellent absorbance of light with i-line wavelength (365 nm), has a high solubility in an organic solvent so that a polymeric composition may be prepared easily, and exhibits excellent thermal stability and good acid generation rate, and a photoacid generator and a photoresist composition comprising the same.

BACKGROUND ART

A photoacid generator is a compound that generates an acid by light irradiation, and the acid generated therefrom—according to the components in a photoresist composition—decomposes a part of the components in the composition or causes crosslinking reaction, to generate change in polarity of polymer in the composition. Such a change in polarity of polymer brings difference in solubility to developer solution between the exposed part and the unexposed part, and as a result, positive or negative lithography becomes possible.

For a photoresist composition, the photoacid generator therein should have good energy sensitivity to the irradiated light so that micropatterns can be formed. However, use of conventional photoacid generator alone has a problem that the sensitivity of photoresist cannot be increased satisfactorily.

Therefore, it is necessary to develop a photoacid generator which has excellent photosensitivity so as to realize sufficient sensitivity even with a small amount, and thus can reduce exposure dose and increase production due to cost reduction and excellent sensitivity. In addition, improvement in solubility of photoacid generator to the main solvent of photoresist has the advantage of facilitating preparation of various compositions.

Various developments for naphthalimide compound have been made in order to increase photosensitivity and improve solubility thereof. For instance, Korean Laid-open Patent Publication No. 10-2017-0125980 discloses preparation of naphthalimide compound by using a cryogenic condition of −70° C. and metal compound such as 1-butyl lithium, and Korean Laid-open Patent Publication No. 10-2017-0042726 and Korean Laid-open Patent Publication No. 10-2012-0114353 disclose preparation of naphthalimide compound by using bromine-substituted compound.

PROBLEMS TO BE SOLVED

The purpose of the present invention is to provide a sulfonic acid derivative compound of naphthalimide which has an excellent photosensitivity suitable as photoacid generator used for photolithography and a high solubility in an organic solvent, and exhibits excellent thermal stability and good acid generation rate, and a photoacid generator and a photoresist composition comprising the same.

TECHNICAL MEANS

In order to achieve the above-stated purpose, the P t aspect of the present invention provides a sulfonic acid derivative compound of naphthalimide represented by the following Formula I:

[Formula I]

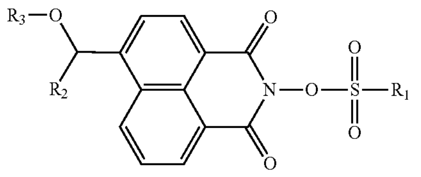

wherein $R_1$ and $R_2$ are each independently a substituted or unsubstituted aliphatic hydrocarbon group, a substituted or unsubstituted aryl group, a substituted or unsubstituted arylalkyl group, or a substituted or unsubstituted alkylaryl group; and $R_3$ is independently a substituted or unsubstituted aliphatic hydrocarbon group, a substituted or unsubstituted aryl group, a substituted or unsubstituted arylalkyl group, a substituted or unsubstituted alkylaryl group, or a group of formula $R_4$—O—$(CH_2)_n$—, where n is an integer of 1 to 12 and $R_4$ is a substituted or unsubstituted aliphatic hydrocarbon group.

The 2nd aspect of the present invention provides a photoacid generator comprising the sulfonic acid derivative compound of naphthalimide according to the present invention.

The 3rd aspect of the present invention provides a photoresist composition comprising the sulfonic acid derivative compound of naphthalimide according to the present invention; and a binder resin.

Other aspects of the present invention provide a substrate coated with the photoresist composition according to the present invention; a patterned substrate obtained by exposing and developing the coated substrate; a display device comprising the patterned substrate; and a semiconductor device comprising the patterned substrate.

EFFECT OF THE INVENTION

The sulfonic acid derivative compound of naphthalimide according to the present invention has high solubility in a solvent for photoresist, excellent thermal stability, and very excellent sensitivity to light for photoresist (for example, light with i-line wavelength (365 nm)), and thus, when used as a photoacid generator component in a photoresist composition, it can provide patterns having excellent developability, taper angle, pattern stability, etc. even with a small amount of use, and it also can minimize the outgassing generated from photoacid generator in exposure and post-bake processes, and so it can reduce pollution and has the advantage of minimizing defects that may be generated thereby.

CONCRETE MODE FOR CARRYING OUT THE INVENTION

The present invention is explained in more detail below.

The sulfonic acid derivative compound of naphthalimide according to the present invention is represented by the following Formula I:

[Formula I]

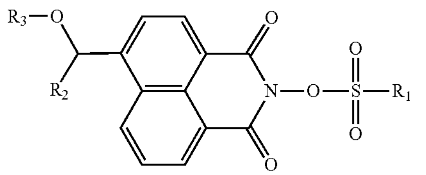

wherein $R_1$ and $R_2$ are each independently a substituted or unsubstituted aliphatic hydrocarbon group, a substituted or unsubstituted aryl group, a substituted or unsubstituted arylalkyl group, or a substituted or unsubstituted alkylaryl group; and $R_3$ is independently a substituted or unsubstituted aliphatic hydrocarbon group, a substituted or unsubstituted aryl group, a substituted or unsubstituted arylalkyl group, a substituted or unsubstituted alkylaryl group, or a group of formula $R_4$—O—$(CH_2)_n$—, where n is an integer of 1 to 12 and $R_4$ is a substituted or unsubstituted aliphatic hydrocarbon group.

More concretely, in Formula I, $R_1$ and $R_2$ may be each independently a substituted or unsubstituted, $C_1$-$C_{12}$ linear alkyl group or $C_3$-$C_{12}$ branched alkyl group; a substituted or unsubstituted $C_3$-$C_{12}$ alicyclic hydrocarbon group; a substituted or unsubstituted $C_6$-$C_{20}$ aryl group; a substituted or unsubstituted $C_7$-$C_{20}$ arylalkyl group; or a substituted or unsubstituted $C_7$-$C_{20}$ alkylaryl group; and $R_3$ may be a substituted or unsubstituted, $C_1$-$C_{12}$ linear alkyl group or $C_3$-$C_{12}$ branched alkyl group; a substituted or unsubstituted $C_3$-$C_{12}$ alicyclic hydrocarbon group; a substituted or unsubstituted $C_6$-$C_{20}$ aryl group; a substituted or unsubstituted $C_7$-$C_{20}$ arylalkyl group; a substituted or unsubstituted $C_7$-$C_{20}$ alkylaryl group; or a substituted or unsubstituted $C_1$-$C_{12}$ alkoxy-$C_1$-$C_{12}$ alkyl group.

Still more concretely, in Formula I, $R_1$ and $R_2$ may be each independently a $C_1$-$C_{12}$ linear alkyl group or $C_3$-$C_{12}$ branched alkyl group which is unsubstituted or substituted with one or more halogen atoms or alicyclic hydrocarbon groups; a $C_3$-$C_{12}$ alicyclic hydrocarbon group which is unsubstituted or substituted with one or more halogen atoms; a $C_6$-$C_{20}$ aryl group which is unsubstituted or substituted with one or more halogen atoms; a $C_7$-$C_{20}$ arylalkyl group which is unsubstituted or substituted with one or more halogen atoms or $C_1$-$C_{12}$ alkylthio groups; or a $C_7$-$C_{20}$ alkylaryl group which is unsubstituted or substituted with one or more halogen atoms; and $R_3$ may be a $C_1$-$C_{12}$ linear alkyl group or $C_3$-$C_{12}$ branched alkyl group which is unsubstituted or substituted with one or more halogen atoms or alicyclic hydrocarbon groups; a $C_3$-$C_{12}$ alicyclic hydrocarbon group which is unsubstituted or substituted with one or more halogen atoms; a $C_6$-$C_{20}$ aryl group which is unsubstituted or substituted with one or more halogen atoms; a $C_7$-$C_{20}$ arylalkyl group which is unsubstituted or substituted with one or more halogen atoms or $C_1$-$C_{12}$ alkylthio groups; a $C_7$-$C_{20}$ alkylaryl group which is unsubstituted or substituted with one or more halogen atoms; or a $C_1$-$C_{12}$ alkoxy-$C_1$-$C_4$ alkyl group which is unsubstituted or substituted with one or more halogen atoms.

Still more concretely, in Formula I, $R_1$ may be methyl group, ethyl group, trifluoromethyl group, 2,2,2-trifluoroethyl group, nonafluorobutyl group or tosyl group;

$R_2$ may be methyl group, ethyl group, propyl group, isopropyl group, butyl group or cyclohexyl group; and $R_3$ may be methyl group, ethyl group, propyl group, hexyl group, heptyl group, cyclohexyl group, methoxyethyl group or butoxyethyl group.

In the present invention, a substituent comprising "alkyl" moiety includes all forms of linear type or branched type, and "cycloalkyl" includes hydrocarbons of not only single ring system but also multi-ring system. In the present invention, "aryl" is an organic radical derived from aromatic hydrocarbon by removing therefrom one hydrogen, and it includes a single or fused ring system containing suitably 4 to 7, preferably 5 or 6 ring atoms in each ring, and even a form of plural aryls connected by single bonds. Also, in the present invention, $C_1$-$C_{12}$ alkyl group may be more concretely $C_1$-$C_{10}$ alkyl and still more concretely $C_1$-$C_6$ alkyl; $C_6$-$C_{20}$ aryl group may be more concretely $C_6$-$C_{18}$ aryl; and $C_3$-$C_{12}$ cycloalkyl group may be more concretely $C_3$-$C_{10}$ cycloalkyl.

In an embodiment, the sulfonic acid derivative compound of naphthalimide according to the present invention may be selected from the following compounds, but it is not especially limited thereto.

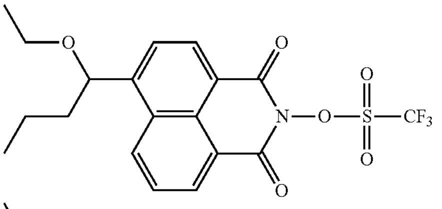

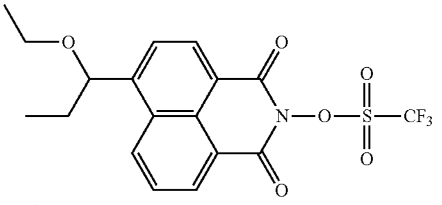 [SMILES: CCOC(CC)c1ccc2c3c(cccc13)C(=O)N(OS(=O)(=O)C(F)(F)F)C2=O]

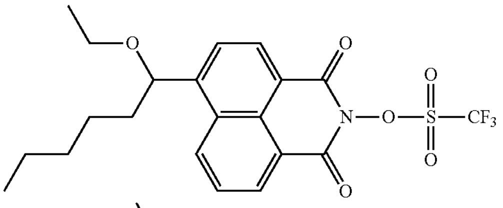

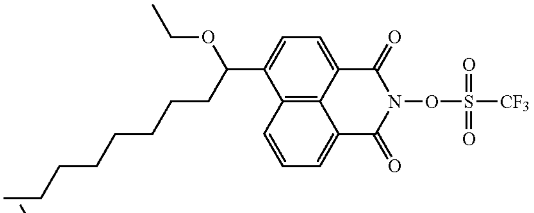

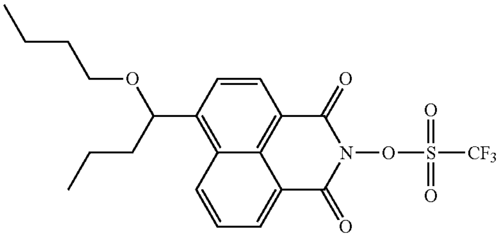

-continued
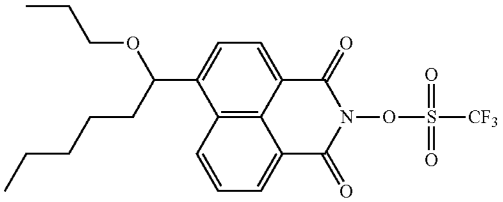
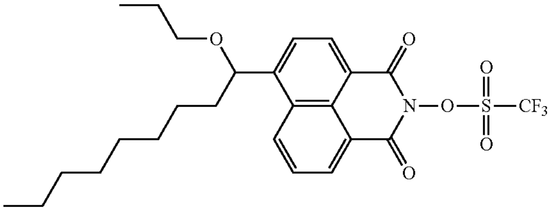
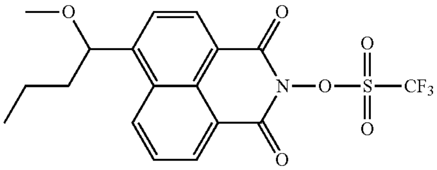
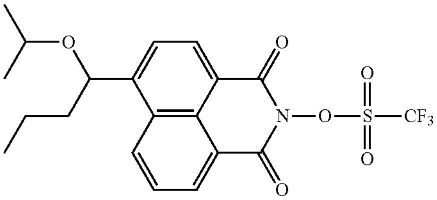
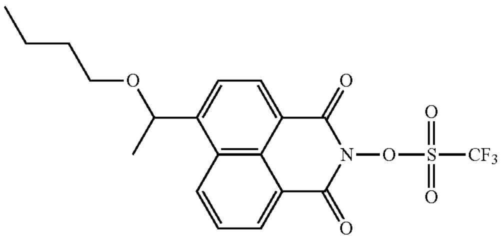
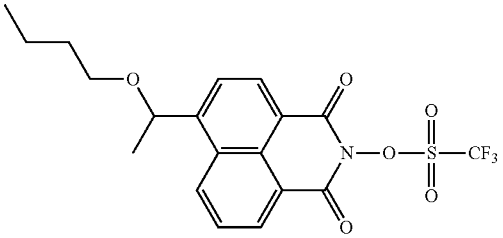
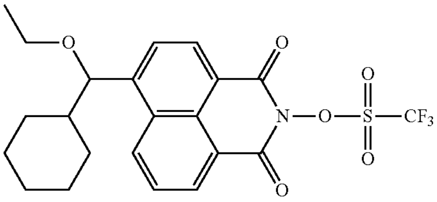
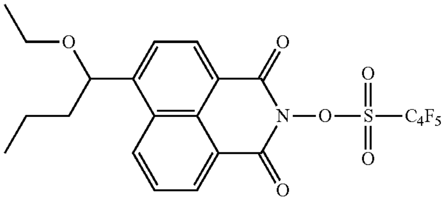
-continued
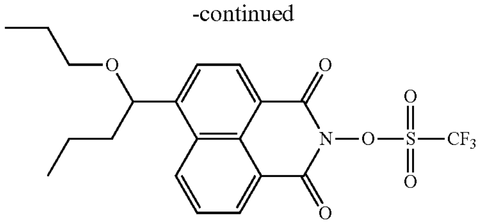
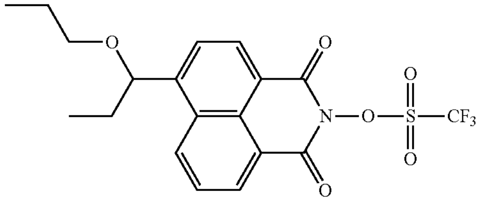
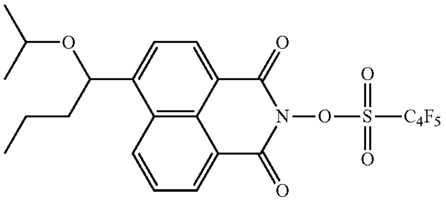
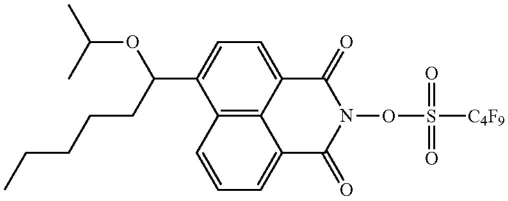
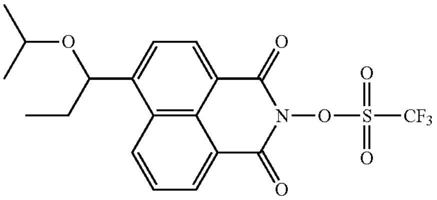
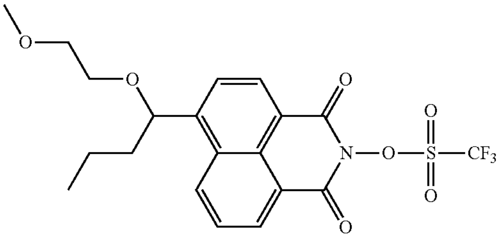
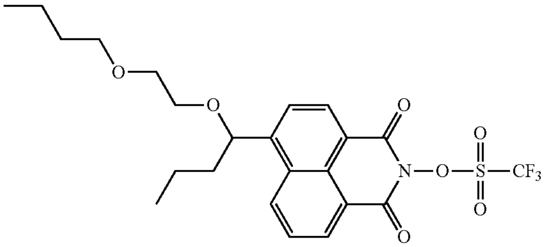
In an embodiment, the sulfonic acid derivative compound of naphthalimide represented by the above Formula I according to the present invention may be prepared via a route as shown in Reaction Scheme 1 below, but it is not limited thereto:

[Reaction Scheme 1]

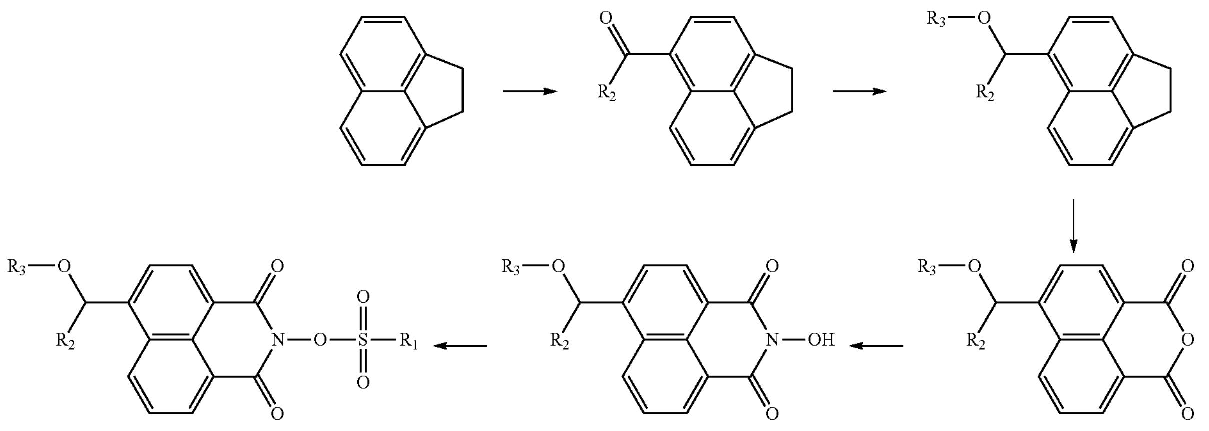

[In Reaction Scheme 1 above, $R_1$ to $R_3$ are the same as defined in Formula I above.]

Since the sulfonic acid derivative compound of naphthalimide according to the present invention has high solubility in a solvent for photoresist, excellent thermal stability, and very excellent sensitivity to light for photoresist, it is very useful as a photoacid generator component in a photoresist composition.

Therefore, other aspects of the present invention provide a photoacid generator and a photoresist composition comprising the sulfonic acid derivative compound of naphthalimide according to the present invention.

The photoresist composition of the present invention comprises the sulfonic acid derivative compound of naphthalimide according to the present invention; and a binder resin, wherein the sulfonic acid derivative compound of naphthalimide is comprised as a component for photoacid generation.

In an embodiment, the binder resin may be selected from, for example, polymers of hydroxystyrene or derivatives thereof; polymers of acrylic acid or derivatives thereof; polymers of methacrylic acid or derivatives thereof; copolymers of two or more monomers selected from hydroxystyrene, acrylic acid, methacrylic acid, and derivatives thereof; copolymers of two or more monomers selected from hydroxystyrene, styrene, and derivatives thereof; copolymers of three or more monomers selected from cycloolefins, maleic anhydride, acrylic acid, and derivatives thereof; copolymers of three or more monomers selected from cycloolefins, maleimides, acrylic acid, and derivatives thereof; polynorbornene; metathesis ring-opening polymers; and polymers partially substituted with acid labile group having alkali dissolution control ability in said polymers; and combinations thereof, but it is not especially limited thereto. Examples of the acid labile group incorporated into the polymer may include tertiary alkyl group, trialkylsilyl group, oxoalkyl group, aryl-substituted alkyl group, heteroalicyclic group such as tetrahydropyran-2-yl group, etc., tertiary alkylcarbonyl group, tertiary alkylcarbonylalkyl group, alkyloxycarbonyl groups, etc.

In an embodiment, the binder resin may be selected from, for example, polymers of hydroxystyrene or derivatives thereof; polymers of acrylic acid or derivatives thereof; polymers of methacrylic acid or derivatives thereof; copolymers of two or more monomers selected from hydroxystyrene, acrylic acid, methacrylic acid, and derivatives thereof; copolymers of two or more monomers selected from hydroxystyrene, styrene, and derivatives thereof; copolymers of three or more monomers selected from hydroxystyrene, styrene, acrylic acid, olefins, cycloolefins, maleic anhydride and derivatives thereof; and combinations thereof, but it is not especially limited thereto.

In an embodiment, said "derivative" may be, for example, alkyl or alkoxy-substituted form (more concretely, $C_1$-$C_{10}$ alkyl or alkoxy-substituted form) of the original compound, or if the original compound is an acid compound, it may be alkyl ester (more concretely, $C_1$-$C_{10}$ alkyl ester) of the original compound, but it is not especially limited thereto.

In an embodiment, the binder resin may be, for example, a copolymer of two or more monomers selected from the following monomers:

methyl (meth)acrylate, ethyl (meth)acrylate, propyl (meth)acrylate, butyl (meth)acrylate, pentyl(meth)acrylate, hexyl (meth)acrylate, cyclohexyl (meth)acrylate, heptyl (meth)acrylate, octyl (meth)acrylate, nonyl (meth)acrylate, decyl (meth)acrylate, lauryl (meth)acrylate, dodecyl (meth) acrylate, tetradecyl (meth)acrylate hexadecyl (meth)acrylate, isobornyl (meth)acrylate, adamantyl (meth)acrylate, dicyclopentanyl (meth)acrylate, dicyclopentenyl (meth) acrylate, benzyl (meth)acrylate, 2-methoxyethyl (meth) acrylate, 2-ethoxyethyl (meth)acrylate, acrylic acid, methacrylic acid, itaconic acid, maleic acid, maleic anhydride, maleic acid monoalkyl ester, monoalkyl itaconate, monoalkyl fumarate, glycidyl acrylate, glycidyl methacrylate, 3,4-epoxybutyl (meth)acrylate, 2,3-epoxycyclohexyl (meth) acrylate, 3,4-epoxycyclohexylmethyl (meth)acrylate, 3-methyloxetane-3-methyl (meth)acrylate, 3-ethyloxetane-3-methyl (meth)acrylate, etc. and styrene, α-methylstyrene, acetoxystyrene, N-methylmaleimide, N-ethylmaleimide, N-propylmaleimide, N-butylmaleimide, N-cyclohexylmaleimide, (meth)acrylamide, N-methyl (meth)acrylamide.

In an embodiment, the binder resin may be a polymer having acryl unsaturated bond in its side chain, and this may be, for example, a copolymer obtained by addition reaction of epoxy compound to a copolymer containing carboxylic acid.

More concretely, the copolymer containing carboxylic acid may be obtained by copolymerizing a monomer containing carboxylic acid such as acrylic acid, methacrylic acid, itaconic acid, maleic acid, maleic acid monoalkyl ester, etc. and one or monomers of alkyl (meth)acrylates such as methyl (meth)acrylate, hexyl (meth)acrylate, etc., cyclohexyl (meth)acrylate, isobornyl (meth)acrylate, adamantyl (meth)acrylate, dicyclopentanyl (meth)acrylate, dicyclopentenyl (meth)acrylate, benzyl (meth)acrylate, 2-methoxyethyl (meth)acrylate, 2-ethoxyethyl (meth)acrylate, styrene, α-methylstyrene, acetoxystyrene, N-methylmaleimide, N-ethylmaleimide, N-propylmaleimide, N-butylmaleimide, N-cyclohexylmaleimide, (meth)acrylamide, N-methyl (meth)acryl amide, etc., and a copolymer obtained by addition reaction of epoxy compound such as glycidyl acrylate, glycidyl methacrylate, 3,4-epoxybutyl (meth)acrylate, 2,3-epoxycyclohexyl (meth)acrylate, 3,4-epoxycyclohexylmethyl (meth)acrylate, etc. to such a carboxylic acid-containing copolymer at a temperature of 40 to 180° C. may be used as the binder resin.

In an embodiment, the weight average molecular weight of the binder resin may be 2,000 to 300,000 and more concretely 4,000 to 100,000, and dispersity thereof may be 1 to 10, but it is not especially limited thereto.

In an embodiment, in order to increase developability and minimize exposure dose, the sulfonic acid derivative compound of naphthalimide used as an acid generator may be comprised, based on 100 weight % of the photoresist composition of the present invention, in an amount of: 0.01 to 10 weight %, 0.01 to 9 weight %, 0.01 to 8 weight %, 0.01 to 7 weight %, 0.01 to 6 weight %, 0.01 to 5 weight %, 0.01 to 4 weight %, 0.01 to 3 weight %, 0.01 to 2 weight %, 0.01 to 1 weight %, 0.01 to 0.5 weight %, 0.01 to 0.4 weight %, 0.01 to 0.35 weight %, 0.01 to 0.3 weight %, 0.01 to 0.2 weight %, 0.05 to 10 weight %, 0.05 to 9 weight %, 0.05 to 8 weight %, 0.05 to 7 weight %, 0.05 to 6 weight %, 0.05 to 5 weight %, 0.05 to 4 weight %, 0.05 to 3 weight %, 0.05 to 2 weight %, 0.05 to 1 weight %, 0.05 to 0.5 weight %, 0.05 to 0.4 weight %, 0.05 to 0.35 weight %, 0.05 to 0.3 weight %, 0.05 to 0.2 weight %, 0.1 to 10 weight %, 0.1 to 9 weight %, 0.1 to 8 weight %, 0.1 to 7 weight %, 0.1 to 6 weight %, 0.1 to 5 weight %, 0.1 to 4 weight %, 0.1 to 3 weight %, 0.1 to 2 weight %, 0.1 to 1 weight %, 0.1 to 0.5 weight %, 0.1 to 0.4 weight %, 0.1 to 0.35 weight %, 0.1 to 0.3 weight %, 0.1 to 0.2 weight %, 0.2 to 10 weight %, 0.2 to 9 weight %, 0.2 to 8 weight %, 0.2 to 7 weight %, 0.2 to 6 weight %, 0.2 to 5 weight %, 0.2 to 4 weight %, 0.2 to 3 weight %, 0.2 to 2 weight %, 0.2 to 1 weight %, 0.2 to 0.5 weight %, 0.2 to 0.4 weight %, 0.2 to 0.35 weight %, 0.2 to 0.3 weight %, 0.25 to 10 weight %, 0.25 to 9 weight %, 0.25 to 8 weight %, 0.25 to 7 weight %, 0.25 to 6 weight %, 0.25 to 5 weight %, 0.25 to 4 weight %, 0.25 to 3 weight %, 0.25 to 2 weight %, 0.25 to 1 weight %, 0.25 to 0.5 weight %, 0.25 to 0.4 weight %, 0.25 to 0.35 weight %, 0.25 to 0.3 weight %, 0.3 to 10 weight %, 0.3 to 9 weight %, 0.3 to 8 weight %, 0.3 to 7 weight %, 0.3 to 6 weight %, 0.3 to 5 weight %, 0.3 to 4 weight %, 0.3 to 3 weight %, 0.3 to 2 weight %, 0.3 to 1 weight %, 0.3 to 0.5 weight %, 0.3 to 0.4 weight %, 0.3 to 0.35 weight %, 0.35 to 10 weight %, 0.35 to 9 weight %, 0.35 to 8 weight %, 0.35 to 7 weight %, 0.35 to 6 weight %, 0.35 to 5 weight %, 0.35 to 4 weight %, 0.35 to 3 weight %, 0.35 to 2 weight %, 0.35 to 1 weight %, 0.35 to 0.5 weight %, 0.35 to 0.4 weight %, 0.4 to 10 weight %, 0.4 to 9 weight %, 0.4 to 8 weight %, 0.4 to 7 weight %, 0.4 to 6 weight %, 0.4 to 5 weight %, 0.4 to 4 weight %, 0.4 to 3 weight %, 0.4 to 2 weight %, 0.4 to 1 weight %, 0.4 to 0.5 weight %, and more concretely in an amount of 0.1 to 5 weight %, but it is not especially limited thereto.

In an embodiment, in order to control pattern characteristics and give thin film properties, the binder resin may be comprised, based on 100 weight % of the photoresist composition of the present invention, in an amount of: for example, 30 to 99 weight %, 35 to 99 weight %, 40 to 99 weight %, 45 to 99 weight %, 50 to 99 weight %, 30 to 97 weight %, 35 to 97 weight %, 40 to 97 weight %, 45 to 97 weight %, 50 to 97 weight %, 30 to 95 weight %, 35 to 95 weight %, 40 to 95 weight %, 45 to 95 weight %, 50 to 95 weight %, 30 to 93 weight %, 35 to 93 weight %, 40 to 93 weight %, 45 to 93 weight %, 50 to 93 weight %, 30 to 90 weight %, 35 to 90 weight %, 40 to 90 weight %, 45 to 90 weight %, 50 to 90 weight %, 30 to 85 weight %, 35 to 85 weight %, 40 to 85 weight %, 45 to 85 weight %, 50 to 85 weight %, 30 to 80 weight %, 35 to 80 weight %, 40 to 80 weight %, 45 to 80 weight %, 50 to 80 weight %, 30 to 75 weight %, 35 to 75 weight %, 40 to 75 weight %, 45 to 75 weight %, 50 to 75 weight %, 30 to 70 weight %, 35 to 70 weight %, 40 to 70 weight %, 45 to 70 weight %, 50 to 70 weight %, 30 to 65 weight %, 35 to 65 weight %, 40 to 65 weight %, 45 to 65 weight %, 50 to 65 weight %, 30 to 60 weight %, 35 to 60 weight %, 40 to 60 weight %, 45 to 60 weight %, 50 to 60 weight %, 30 to 55 weight %, 35 to 55 weight %, 40 to 55 weight %, 45 to 55 weight %, 50 to 55 weight %, and more concretely in an amount of 50 to 99 weight %, but it is not especially limited thereto.

The photoresist composition of the present invention may further comprise a solvent.

As the solvent, considering compatibility with the photoacid generator and other compounds, a solvent such as ethyl acetate, butyl acetate, diethylene glycol dimethyl ether, diethylene glycol methyl ethyl ether, methyl methoxy propionate, ethyl ethoxy propionate (EEP), ethyl lactate, propylene glycol monomethyl ether acetate (PGMEA), propylene glycol methyl ether propionate (PGMEP), propylene glycol methyl ether, propylene glycol propyl ether, methyl cellosolve acetate, ethyl cellosolve acetate, diethylene glycol methyl acetate, diethylene glycol ethyl acetate, acetone, methyl isobutyl ketone, cyclohexanone, dimethylformamide (DMF), N,N-dimethylacetamide (DMAc), N-methyl-2-pyrrolidone (NMP), γ-butyrolactone, diethyl ether, ethylene glycol dimethyl ether, diglyme, tetrahydrofuran (THF), methanol, ethanol, propanol, iso-propanol, methyl cellosolve, ethyl cellosolve, diethylene glycol methyl ether, diethylene glycol ethyl ether, dipropylene glycol methyl ether, toluene, xylene, hexane, heptane, octane, etc. may be used alone or in a mixture of two or more thereof.

In an embodiment, in order to adjust the viscosity of the composition to be in the range of 1 to 50 cps, the solvent may be contained, for example, in an amount of 0.9 to 60 weight % in 100 weight % of the photoresist composition of the present invention, but it is not especially limited thereto.

If necessary, the photoresist composition of the present invention may further comprise an additive with compatibility such as defoaming agent, leveling agent, etc.

Still other aspects of the present invention provide a substrate coated with the photoresist composition according to the present invention; a patterned substrate obtained by exposing and developing the coated substrate; a display device comprising the patterned substrate; and a semiconductor device comprising the patterned substrate.

In an embodiment, the substrate may be, for example, a silicon wafer substrate, the coating of the photoresist composition may be conducted, for example, by a known method such as spin coating, the exposure may be conducted, for example, by using light with i-line wavelength (365 nm), and the development may be conducted, for example, by using a basic developer solution such as an aqueous solution of trimethylammonium hydroxide (TMAH), but it is not limited thereto.

The present invention is explained in more detail through the following Examples. However, the scope of the present invention is not limited thereby in any manner.

EXAMPLES

Example 1: Preparation of 4-(1-ethoxybutyl)-naphthalimide trifluoromethane sulfonate (1)

Reaction 1. Synthesis of 5-butyryl acenaphthene 21.43 g (139.0 mmol) of acenaphthene was added to dichloromethane, and cooled to 10° C. or lower. 19.46 g (145.9 mmol) of aluminum chloride was added thereto and stirred for 30 minutes, and then 14.81 g (139.0 mmol) of butyryl chloride was slowly added thereto, and the reaction mixture was stirred for 1 hour at 5° C. or lower. Next, distilled water was added to the reaction product, and after stirring for 30 minutes, the organic layer was separated. The separated organic layer was washed twice with distilled water, and the collected organic layer was dried with anhydrous magnesium sulfate, and the solvent was removed by distillation under reduced pressure. The concentrated residue was purified by silica gel column chromatography (developing solvent; ethyl acetate:n-heptane=1:4) to obtain 21.90 g (70.26%) of 5-butyryl acenaphthene.

$^1$H NMR ($\delta_{ppm}$; $CDCl_3$): δ 8.65-8.62 (dd, 1H), 8.05-8.02 (d, 1H), 7.66-7.55 (dd, 1H), 7.41-7.35 (d, 1H), 7.31-7.29 (dd, 1H), 3.43-3.38 (m, 4H), 3.05 (t, 2H), 1.87-1.77 (m, 2H), 1.04 (t, 3H)

MS(m/z): 224

Reaction 2. Synthesis of 5-(1-ethoxybutyl)acenaphthene 10.60 g (47.3 mmol) of 5-butyryl acenaphthene was dissolved in ethanol and sodium borohydride was added thereto, the mixture was stirred at 60° C. and then cooled to 10° C. or lower, and 19.17 mL of 10% aqueous solution of hydrochloric acid was slowly added thereto and the mixture was stirred at 60° C. After the reaction was finished, distilled water was added to the reaction product and stirred for 30 minutes. Next, ethyl acetate was added thereto and the mixture was stirred, and then the organic layer was separated. The separated organic layer was washed with each of saturated aqueous solution of sodium bicarbonate and distilled water, and the collected organic layer was dried with anhydrous magnesium sulfate, and the solvent was removed by distillation under reduced pressure. The product obtained by distilling the organic layer under reduced pressure was purified by silica gel column chromatography (developing solvent: ethyl acetate:n-heptane=1:10) to obtain 9.54 g (79.3%) of 5-(1-ethoxybutyl) acenaphthene.

$^1$H NMR ($\delta_{ppm}$; $CDCl_3$): δ 7.91 (d, 1H), 7.45 (dt, 2H), 7.31-7.25 (m, 2H), 4.86 (dd, 1H), 3.45-3.34 (m, 6H), 1.95 (m, 1H), 1.83 (m, 1H), 1.56-1.45 (m, 1H), 1.39-1.30 (m, 1H), 1.20 (t, 3H), 0.93 (t, 3H)

MS(m/z): 254

Reaction 3. Synthesis of 4-(1-ethoxybutyl)naphthalic anhydride 7.24 g (28.4 mmol) of 5-(1-ethoxybutyl) acenaphthene was added to acetic acid, 42.41 g (142.3 mmol) of sodium dichromate dihydrate was added thereto, and the mixture was stirred at room temperature and heated to reflux. Then, after cooling to room temperature, the reaction mixture was poured into ice water, and ethyl acetate was added thereto and the mixture was stirred for 30 minutes. The organic layer was separated and washed with each of saturated aqueous solution of sodium bicarbonate and distilled water, and the collected organic layer was dried with anhydrous magnesium sulfate, and the solvent was removed by distillation under reduced pressure. The product obtained by distilling the organic layer under reduced pressure was purified by silica gel column chromatography (developing solvent: ethyl acetate:n-heptane=1:10) to obtain 6.32 g (74.4%) of 4-(1-ethoxybutyl) naphthalic anhydride.

$^1$H NMR ($\delta_{ppm}$; $CDCl_3$): δ 8.73 (dd, 1H), 8.65 (dd, 1H), 8.62 (d, 1H), 7.87 (d, 1H), 7.83 (dd, 1H), 5.00 (dd, 1H), 3.46-3.38 (m, 2H), 1.99-1.87 (m, 1H), 1.84-1.73 (m, 1H), 1.61-1.56 (m, 1H), 1.54-1.35 (m, 1H), 1.23 (t, 3H), 0.95 (t, 3H)

MS(m/z): 298

Reaction 4. Synthesis of N-hydroxy-4-(1-ethoxybutyl)naphthalimide 4.60 g (15.4 mmol) of 4-(1-ethoxybutyl) naphthalic anhydride was added to ethanol, 1.61 g (23.1 mmol) of hydroxylamine hydrochloride salt and 1.83 g (23.1 mmol) of pyridine were added thereto, and the mixture was heated to reflux. Ethanol was removed under reduced pressure to obtain 4.18 g (crude yield: 86.5%) of crude N-hydroxy-4-(1-ethoxybutyl) naphthalimide, which was used in the next reaction without further purification.

$^1$H NMR ($\delta_{ppm}$; $CDCl_3$): δ 8.71-8.64 (m, 4H), 7.86 (d, 1H), 7.81 (dd, 1H), 5.00 (dd, 1H), 3.46-3.38 (m, 2H), 2.02-1.87 (m, 1H), 1.85-1.73 (m, 1H), 1.62-1.50 (m, 1H), 1.46-1.36 (m, 1H), 1.23 (t, 3H), 0.95 (t, 3H)

MS(m/z): 313

Reaction 5. Synthesis of 4-(1-ethoxybutyl)naphthalimide trifluoromethane sulfonate 4.08 g (13.2 mmol) of N-hydroxy-4-(1-ethoxybutyl) naphthalimide was added to dichloromethane, and 2.64 g (26.0 mmol) of triethylamine was added thereto, and the mixture was stirred for 30 minutes and cooled to 5° C. or lower. After adding 2.19 g (13.2 mmol) of trifluoromethane sulfonyl chloride, the mixture was stirred at room temperature. Then, after adding thereto distilled water and stirring, the organic layer was separated. The separated organic layer was washed twice with distilled water, and the collected organic layer was dried with anhydrous magnesium sulfate, and the solvent was removed by distillation under reduced pressure. The product obtained by distilling the organic layer under reduced pressure was purified by silica gel column chromatography (developing solvent: ethyl acetate:n-heptane=1:4) to obtain 4.12 g (71.7%) of 4-(1-ethoxybutyl) naphthalimide trifluoromethane sulfonate (1).

$^1$H NMR ($\delta_{ppm}$; $CDCl_3$): δ 8.76 (dd, 1H), 8.71 (dd, 1H), 8.68 (d, 1H), 7.90 (d, 1H), 7.85 (dd, 1H), 5.01 (dd, 1H), 3.49-3.35 (m, 2H), 1.97-1.88 (m, 1H), 1.82-1.74 (m, 1H), 1.62-1.51 (m, 1H), 1.47-1.36 (m, 1H), 1.23 (t, 3H), 0.95 (t, 3H)

MS(m/z): 445

The following compounds were prepared in the same manner as in Example 1.

| Compound No. | Structure | $^1$H-NMR | MS (m/z) |
|---|---|---|---|
| 1 | 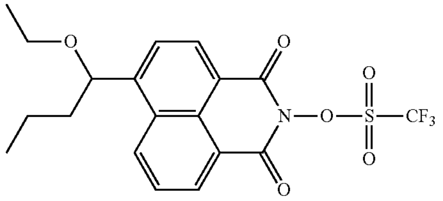 | δ 8.76 (dd, 1H), 8.71 (dd, 1H), 8.68 (d, 1H), 7.90 (d, 1H), 7.85 (dd, 1H), 5.01 (dd, 1H), 3.49-3.35 (m, 2H), 1.97-1.88 (m, 1H), 1.82-1.74 (m, 1H), 1.62-1.51 (m, 1H), 1.47-1.36 (m, 1H), 1.23 (t, 3H), 0.95 (t, 3H) | 445 |
| 2 | 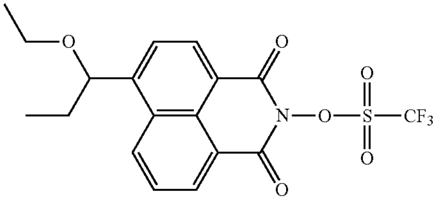 | δ 8.77 (dd, 1H), 8.71 (dd, 1H), 8.68 (d, 1H), 7.94 (d, 1H), 7.85 (dd, 1H), 5.10 (dd, 1H), 3.50-3.36 (m, 2H), 1.82-1.74 (m, 1H), 1.62-1.51 (m, 1H), 1.23 (t, 3H), 0.95 (t, 3H). | 431 |
| 3 | 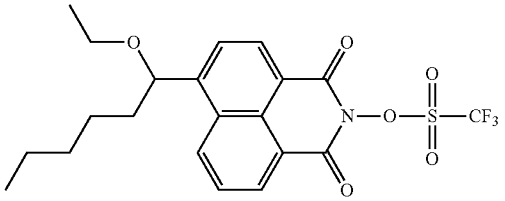 [SMILES: CCCCCC(OCC)c1ccc2c3c(cccc13)C(=O)N(OS(=O)(=O)C(F)(F)F)C2=O] | δ 8.76 (dd, 1H), 8.71 (dd, 1H), 8.68 (d, 1H), 7.90 (d, 1H), 7.85 (dd, 1H), 5.01 (dd, 1H), 3.49-3.35 (m, 2H), 1.97-1.88 (m, 1H), 1.82-1.74 (m, 1H), 1.62-1.51 (m, 1H), 1.47-1.36 (m, 1H), 1.23 (t, 3H), 0.93-0.87 (m, 7H). | 473 |
| 4 | 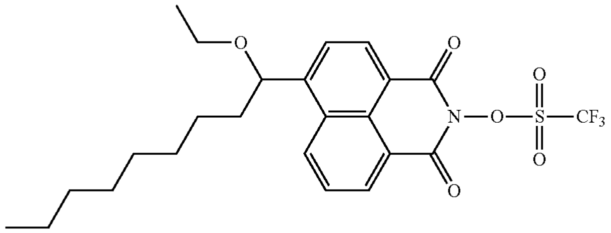 [SMILES: CCCCCCCCC(OCC)c1ccc2c3c(cccc13)C(=O)N(OS(=O)(=O)C(F)(F)F)C2=O] | δ 8.76 (dd, 1H), 8.71 (dd, 1H), 8.68 (d, 1H), 7.90 (d, 1H), 7.85 (dd, 1H), 5.01 (dd, 1H), 3.49-3.35 (m, 2H), 1.97-1.88 (m, 1H), 1.82-1.74 (m, 1H), 1.62-1.51 (m, 1H), 1.47-1.36 (m, 1H), 1.23 (t, 3H), 0.93-0.86 (m, 11H). | 515 |
| 5 | 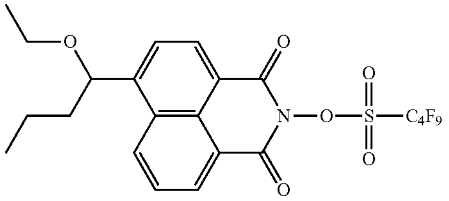 | δ 8.76 (dd, 1H), 8.71 (dd, 1H), 8.68 (d, 1H), 7.90 (d, 1H), 7.85 (dd, 1H), 5.01 (dd, 1H), 3.49-3.35 (m, 2H), 1.97-1.88 (m, 1H), 1.82-1.74 (m, 1H), 1.62-1.51 (m, 1H), 1.47-1.36 (m, 1H), 1.23 (t, 3H), 0.95 (t, 3H). | 595 |
| 6 | 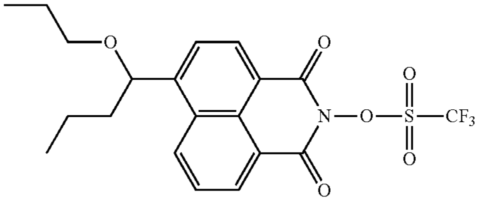 [SMILES: CCCOC(CCC)c1ccc2c3c(cccc13)C(=O)N(OS(=O)(=O)C(F)(F)F)C2=O] | δ 8.76 (dd, 1H), 8.71 (dd, 1H), 8.68 (d, 1H), 7.89 (d, 1H), 7.84 (dd, 1H), 4.98 (dd, 1H), 3.39-3.28 (m, 2H), 1.99-1.87 (m, 1H), 1.83-1.72 (m, 1H), 1.63-1.53 (m, 2H), 1.45-1.33 (m, 2H), 0.95 (t, 3H), 0.89 (t, 3H). | 459 |
| 7 | 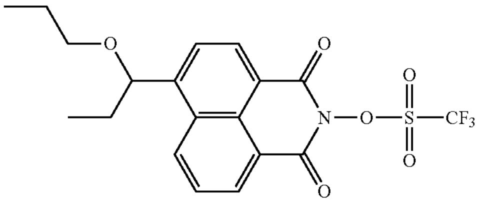 [SMILES: CCCOC(CC)c1ccc2c3c(cccc13)C(=O)N(OS(=O)(=O)C(F)(F)F)C2=O] | δ 8.76 (dd, 1H), 8.71 (dd, 1H), 8.68 (d, 1H), 7.89 (d, 1H), 7.84 (dd, 1H), 4.98 (dd, 1H), 3.39-3.28 (m, 2H), 1.82-1.62 (m, 2H), 1.53-1.33 (m, 2H), 0.95 (t, 3H), 0.89 (t, 3H). | 445 |

-continued
| Compound No. | Structure | $^1$H-NMR | MS (m/z) |
|---|---|---|---|
| 8 | 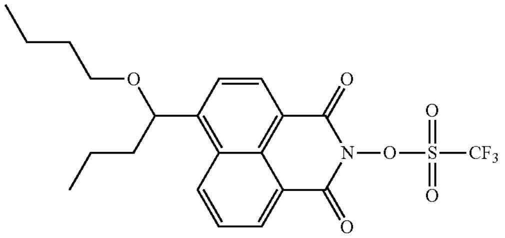 [SMILES: CCCCOC(CCC)c1ccc2c3c(cccc13)C(=O)N(OS(=O)(=O)C(F)(F)F)C2=O] | δ 8.76 (dd, 1H), 8.71 (dd, 1H), 8.68 (d, 1H), 7.89 (d, 1H), 7.84 (dd, 1H), 4.98 (dd, 1H), 3.39-3.28 (m, 2H), 1.99-1.87 (m, 1H), 1.83-1.72 (m, 1H), 1.63-1.53 (m, 3H), 1.45-1.33 (m, 3H), 0.95 (t, 3H), 0.89 (t, 3H). | 473 |
| 9 | 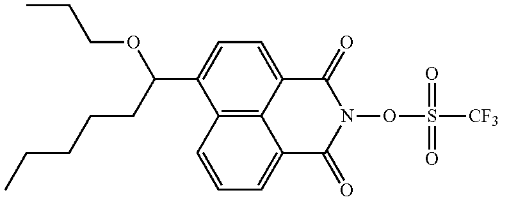 [SMILES: CCCCCC(OCCC)c1ccc2c3c(cccc13)C(=O)N(OS(=O)(=O)C(F)(F)F)C2=O] | δ 8.76 (dd, 1H), 8.71 (dd, 1H), 8.68 (d, 1H), 7.89 (d, 1H), 7.84 (dd, 1H), 4.98 (dd, 1H), 3.39-3.28 (m, 2H), 1.97-1.33 (m, 6H), 0.95 (t, 3H), 0.93-0.87 (m, 7H). | 487 |
| 10 | 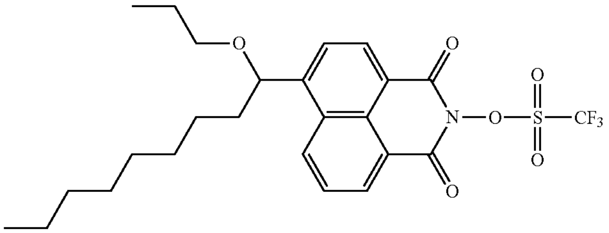 [SMILES: CCCCCCCCC(OCCC)c1ccc2c3c(cccc13)C(=O)N(OS(=O)(=O)C(F)(F)F)C2=O] | δ 8.76 (dd, 1H), 8.71 (dd, 1H), 8.68 (d, 1H), 7.89 (d, 1H), 7.84 (dd, 1H), 4.98 (dd, 1H), 3.39-3.28 (m, 2H), 1.97-1.33 (m, 6H), 0.95 (t, 3H), 0.93-0.86 (m, 11H). | 530 |
| 11 | 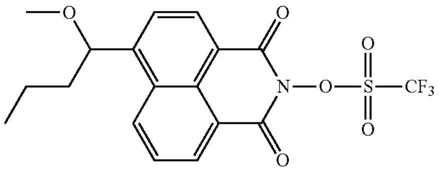 [SMILES: CCCC(OC)c1ccc2c3c(cccc13)C(=O)N(OS(=O)(=O)C(F)(F)F)C2=O] | δ 8.76 (dd, 1H), 8.71 (dd, 1H), 8.68 (d, 1H), 7.90 (d, 1H), 7.85 (dd, 1H), 5.01 (dd, 1H), 3.31(s, 3H), 1.97-1.88 (m, 1H), 1.82-1.74 (m, 1H), 1.62-1.51 (m, 1H), 1.47-1.36 (m, 1H), 0.95 (t, 3H). | 431 |
| 12 | 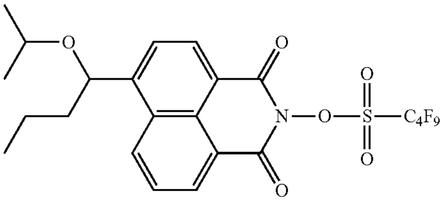 | δ 8.77 (dd, 1H), 8.71 (dd, 1H), 8.68 (d, 1H), 7.94 (d, 1H), 7.85 (dd, 1H), 5.10 (dd, 1H), 3.53-3.46 (m, 1H), 1.94-1.83 (m, 1H), 1.79-1.68 (m, 1H), 1.65-1.55 (m, 1H), 1.48-1.37 (m, 1H), 1.23 (d, 3H), 1.09 (d, 3H), 0.96 (t, 3H). | 609 |
| 13 | 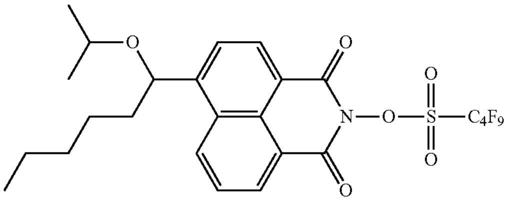 | δ 8.76 (dd, 1H), 8.71 (dd, 1H), 8.68 (d, 1H), 7.90 (d, 1H), 7.85 (dd, 1H), 5.01 (dd, 1H), 3.53-3.46 (m, 1H), 1.97-1.88 (m, 1H), 1.82-1.74 (m, 1H), 1.62-1.51 (m, 1H), 1.47-1.36 (m, 1H), 1.23 (d, 3H), 1.09 (d, 3H), 0.93-0.87 (m, 7H). | 638 |
| 14 | 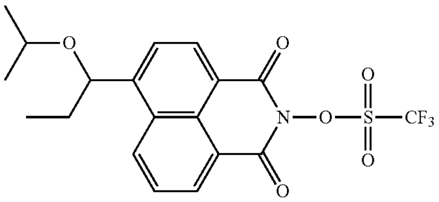 [SMILES: CCC(OC(C)C)c1ccc2c3c(cccc13)C(=O)N(OS(=O)(=O)C(F)(F)F)C2=O] | δ 8.77 (dd, 1H), 8.71 (dd, 1H), 8.68 (d, 1H), 7.94 (d, 1H), 7.85 (dd, 1H), 5.10 (dd, 1H), 3.53-3.46 (m, 1H), 1.94-1.83 (m, 1H), 1.79-1.68 (m, 1H), 1.23 (d, 3H), 1.09 (d, 3H), 0.96 (t, 3H). | 445 |

-continued
| Compound No. | Structure | $^1$H-NMR | MS (m/z) |
|---|---|---|---|
| 15 | 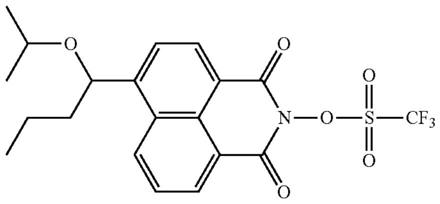 [SMILES: CCCC(OC(C)C)c1ccc2c3c(cccc13)C(=O)N(OS(=O)(=O)C(F)(F)F)C2=O] | δ 8.77 (dd, 1H), 8.71 (dd, 1H), 8.68 (d, 1H), 7.94 (d, 1H), 7.85 (dd, 1H), 5.10 (dd, 1H), 3.53-3.46 (m, 1H), 1.94-1.83 (m, 1H), 1.79-1.68 (m, 1H), 1.65-1.55 (m, 1H), 1.48-1.37 (m, 1H), 1.23 (d, 3H), 1.09 (d, 3H), 0.96 (t, 3H). | 459 |
| 16 | 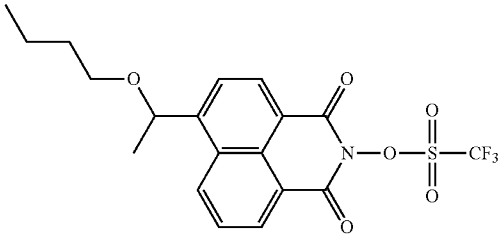 [SMILES: CCCCOC(C)c1ccc2c3c(cccc13)C(=O)N(OS(=O)(=O)C(F)(F)F)C2=O] | δ 8.76 (dd, 1H), 8.71 (dd, 1H), 8.68 (d, 1H), 7.89 (d, 1H), 7.84 (dd, 1H), 4.98 (dd, 1H), 3.39-3.28 (m, 2H), 1.63-1.53 (m, 2H), 1.45-1.33 (m, 2H), 1.29(d, 3H), 0.95 (t, 3H). | 445 |
| 17 | 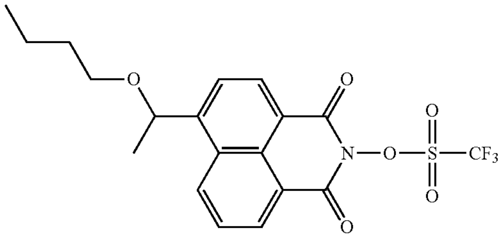 [SMILES: CCCCOC(C)c1ccc2c3c(cccc13)C(=O)N(OS(=O)(=O)C(F)(F)F)C2=O] | δ 8.76 (dd, 1H), 8.71 (dd, 1H), 8.68 (d, 1H), 7.89 (d, 1H), 7.84 (dd, 1H), 4.98 (dd, 1H), 3.39-3.28 (m, 2H), 1.63-1.53 (m, 2H), 1.45-1.33 (m, 2H), 1.29(d, 3H), 0.95 (t, 3H). | 595 |
| 18 | 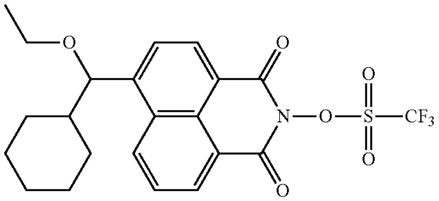 [SMILES: CCOC(c1ccc2c3c(cccc13)C(=O)N(OS(=O)(=O)C(F)(F)F)C2=O)C1CCCCC1] | δ 8.76 (dd, 1H), 8.71 (dd, 1H), 8.68 (d, 1H), 7.90 (d, 1H), 7.85 (dd, 1H), 5.01 (dd, 1H), 3.49-3.35 (m, 2H), 1.75-1.60(m, 6H), 1.23 (t, 3H), 1.21-1.18(m, 5H) | 485 |
| 19 | 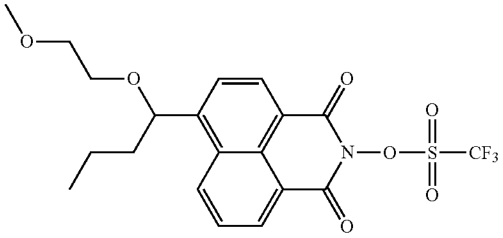 | δ 8.76 (dd, 1H), 8.71 (dd, 1H), 8.68 (d, 1H), 7.90 (d, 1H), 7.85 (dd, 1H), 5.01 (dd, 1H), 3.60-3.52 (m, 4H), 3.36 (s, 3H), 1.97-1.88 (m, 1H), 1.82-1.74 (m, 1H), 1.62-1.51 (m, 1H), 1.47-1.36 (m, 1H), 0.95 (t, 3H). | 475 |
| 20 | 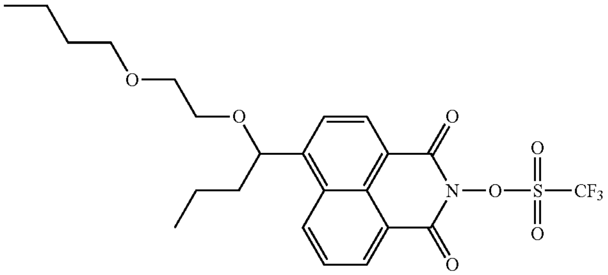 [SMILES: CCCCOCCOC(CCC)c1ccc2c3c(cccc13)C(=O)N(OS(=O)(=O)C(F)(F)F)C2=O] | δ 8.76 (dd, 1H), 8.71 (dd, 1H), 8.68 (d, 1H), 7.90 (d, 1H), 7.85 (dd, 1H), 5.01 (dd, 1H), 3.60-3.52 (m, 4H), 3.43-3.39 (m, 2H), 1.97-1.88 (m, 1H), 1.82-1.74 (m, 1H), 1.62-1.51 (m, 1H), 1.55-1.49(m, 2H), 1.47-1.36 (m, 1H), 1.38-1.30(m, 2H), 0.95 (t, 3H), 0.91(t, 3H). | 517 |

Preparation of Binder Resin a) Preparation of Binder Resin 1

200 ml of propylene glycol monomethyl ether acetate (PGMEA) and 1.5 g of azobisisobutyronitrile (AIBN) were added in a 500 ml polymerization vessel, and acetoxy styrene, styrene, and t-butoxymethacrylate were added with a molar ratio of 50:25:25, respectively, so that the solid content might be 40% by weight, and then polymerized with stirring at 70° C. for 5 hours under nitrogen atmosphere to prepare binder resin 1. It was confirmed that the weight average molecular weight of the copolymer prepared as such was 25,000, and the degree of dispersion thereof was 2.0.

b) Preparation of Binder Resin 2

200 ml of PGMEA and 1.5 g of AIBN were added in a 500 ml polymerization vessel, and acetoxy styrene, styrene, t-butoxymethacrylate and methyl methacrylate were added with a molar ratio of 40:25:25:10, respectively, so that the solid content might be 40% by weight, and then polymerized with stirring at 70° C. for 5 hours under nitrogen atmosphere to synthesize a copolymer. After adding 0.3 g of N,N-dimethylaniline and 20 molar ratio of glycidyl methacrylate to the reactor, the mixture was stirred at 100° C. for 10 hours to prepare binder resin 2, which was an acrylic polymer having an acrylic unsaturated bond in the side chain. It was confirmed that the weight average molecular weight of the copolymer prepared as such was 20,000, and the degree of dispersion thereof was 2.1.

Measurement of Solubility

In preparing a photoresist composition, solubility of a photoacid generator is very important. Hence, the solubility in propylene glycol monomethyl ether (PGMEA) and cyclohexane, which are solvents mainly used in photoresist compositions, were compared with those of the compound of the following Formula II, and are shown in Table 1 below.

[Formula II]

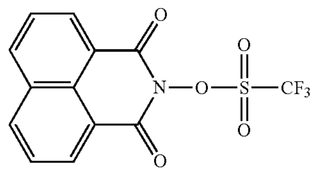

TABLE 1

Solubility of photoacid generators

| Compound No. | Solubility (w/v %) PGMEA | Cyclohexane |
|---|---|---|
| 8 | 50.0 | 62.3 |
| 12 | 9.2 | 25.2 |
| 19 | 60.0 | 64.1 |
| 20 | 45.0 | 54.1 |
| Formula II | 1.7 | 5.8 |

Measurement of Thermal Stability

If a photoacid generator is thermally stable in a photoresist preparation process, a very good effect in terms of stability can be expected. Hence, the temperature at which 5% weight loss occurred was measured by using a thermogravimetric analyzer to compare with the compound of Formula II.

TABLE 2

Thermal stability of photoacid generators

| Compound No. | Temperature at which 5% weight loss occurred (° C.) |
|---|---|
| 8 | 232 |
| 11 | 230 |
| 19 | 234 |
| 20 | 235 |
| Formula V | 223 |

Preparation of Photoresist Compositions of Examples

In a reaction mixing bath equipped with an ultraviolet blocking film and an agitator, according to the components and contents shown in Table 3 below, binder resin 1 or 2; compound 8, 11, 19 or 20 as photoacid generator; and FC-430 (a leveling agent of 3M, 0.02 weight %) were sequentially added, and the mixture was stirred at room temperature, and then PGMEA as a solvent was added to make 100% by weight, to prepare a photoresist composition.

TABLE 3

Preparation of photoresist composition

| Composition No. | Binder resin (parts by weight) | Photoacid generator (parts by weight) | Additive (parts by weight) |
|---|---|---|---|
| 1 | 1 (97) | Compound 8 (0.4) | FC-430 (0.1) |
| 2 | 1 (97) | Compound 11 (0.4) | FC-430 (0.1) |
| 3 | 1 (97) | Compound 19 (0.4) | FC-430 (0.1) |
| 4 | 1 (97) | Compound 20 (0.4) | FC-430 (0.1) |
| 5 | 2 (97) | Compound 8 (0.4) | FC-430 (0.1) |
| 6 | 2 (97) | Compound 11 (0.4) | FC-430 (0.1) |
| 7 | 2 (97) | Compound 19 (0.4) | FC-430 (0.1) |
| 8 | 2 (97) | Compound 20 (0.4) | FC-430 (0.1) |
| 9 | 1 (60) + 2 (37) | Compound 8 (0.4) | FC-430 (0.1) |
| 10 | 1 (37) + 2 (60) | Compound 8 (0.4) | FC-430 (0.1) |

Preparation of Photoresist Composition of Comparative Example

A photoresist composition was prepared in the same manner as in the preparation of Composition 3, except that the photoacid generator of Formula II was used instead of Compound 19 as the photoacid generator.

[Formula II]

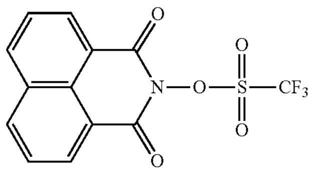

Evaluation of Photoresist Composition

Evaluation of the photoresist compositions of Examples and Comparative Example was performed on a glass substrate, and pattern stability and taper angle of the photoresist composition were measured, and the evaluation results are shown in Table 4 below.

1) Pattern Stability

The photoresist was spin-coated on a silicon wafer substrate, dried on a hot plate at 90° C. for 1 minute, exposed with using a line-space (10 μm-10 μm) step mask, subjected to a post-exposure bake process, and then developed in 2.384% aqueous solution of trimethylammonium hydroxide (TMAH). The width of the pattern in the space portion after the development was measured.

2) Taper Angle

The photoresist was spin-coated on a silicon wafer substrate, dried on a hot plate at 90° C. for 1 minute, exposed with using a line-space (10 μm-10 μm) step mask, subjected to a post-exposure bake process, and then developed in 2.384% aqueous solution of TMAH. The taper angle of the space portion after the development was measured, and it was determined as good in case of 85 to 90°, and poor in case of less than 85° or greater than 91°.

TABLE 4

| Composition No. | Size of space CD pattern (μm) | Value compared with Comparative Example | Condition of taper angle |
|---|---|---|---|
| 1 | 12.3 | 1.06 | Good |
| 2 | 12.1 | 1.04 | Good |
| 3 | 12.2 | 1.05 | Good |
| 4 | 12.1 | 1.04 | Good |
| 5 | 12.0 | 1.03 | Good |
| 6 | 12.2 | 1.05 | Good |
| 7 | 12.1 | 1.04 | Good |
| 8 | 12.0 | 1.03 | Good |
| 9 | 12.2 | 1.05 | Good |
| 10 | 12.0 | 1.03 | Good |
| Comparative Example | 11.6 | 1.00 | Poor |

The invention claimed is:

1. A sulfonic acid derivative compound of naphthalimide represented by the following Formula I:

[Formula I]

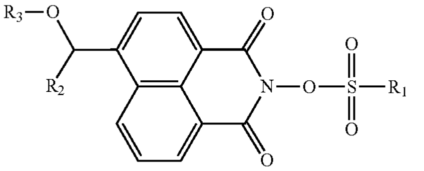

wherein $R_1$ and $R_2$ are each independently a substituted or unsubstituted aliphatic hydrocarbon group, a substituted or unsubstituted aryl group, a substituted or unsubstituted arylalkyl group, or a substituted or unsubstituted alkylaryl group; and $R_3$ is independently a substituted or unsubstituted aliphatic hydrocarbon group, a substituted or unsubstituted aryl group, a substituted or unsubstituted arylalkyl group, a substituted or unsubstituted alkylaryl group, or a group of formula $R_4$—O—$(CH_2)_n$—, where n is an integer of 1 to 12 and $R_4$ is a substituted or unsubstituted aliphatic hydrocarbon group.

2. The sulfonic acid derivative compound of naphthalimide according to claim 1, wherein $R_1$ and $R_2$ are each independently a substituted or unsubstituted, $C_1$-$C_{12}$ linear alkyl group or $C_3$-$C_{12}$ branched alkyl group; a substituted or unsubstituted $C_3$-$C_{12}$ alicyclic hydrocarbon group; a substituted or unsubstituted $C_6$-$C_{20}$ aryl group; a substituted or unsubstituted $C_7$-$C_{20}$ arylalkyl group; or a substituted or unsubstituted $C_7$-$C_{20}$ alkylaryl group; and $R_3$ is a substituted or unsubstituted, $C_1$-$C_{12}$ linear alkyl group or $C_3$-$C_{12}$ branched alkyl group; a substituted or unsubstituted $C_3$-$C_{12}$ alicyclic hydrocarbon group; a substituted or unsubstituted $C_6$-$C_{20}$ aryl group; a substituted or unsubstituted $C_7$-$C_{20}$ arylalkyl group; a substituted or unsubstituted $C_7$-$C_{20}$ alkylaryl group; or a substituted or unsubstituted $C_1$-$C_{12}$ alkoxy-$C_1$-$C_{12}$ alkyl group.

3. The sulfonic acid derivative compound of naphthalimide according to claim 1, wherein $R_1$ and $R_2$ are each independently a $C_1$-$C_{12}$ linear alkyl group or $C_3$-$C_{12}$ branched alkyl group which is unsubstituted or substituted with one or more halogen atoms or alicyclic hydrocarbon groups; a $C_3$-$C_{12}$ alicyclic hydrocarbon group which is unsubstituted or substituted with one or more halogen atoms; a $C_6$-$C_{20}$ aryl group which is unsubstituted or substituted with one or more halogen atoms; a $C_7$-$C_{20}$ arylalkyl group which is unsubstituted or substituted with one or more halogen atoms or $C_1$-$C_{12}$ alkylthio groups; or a $C_7$-$C_{20}$ alkylaryl group which is unsubstituted or substituted with one or more halogen atoms; and $R_3$ is a $C_1$-$C_{12}$ linear alkyl group or $C_3$-$C_{12}$ branched alkyl group which is unsubstituted or substituted with one or more halogen atoms or alicyclic hydrocarbon groups; a $C_3$-$C_{12}$ alicyclic hydrocarbon group which is unsubstituted or substituted with one or more halogen atoms; a $C_6$-$C_{20}$ aryl group which is unsubstituted or substituted with one or more halogen atoms; a $C_7$-$C_{20}$ arylalkyl group which is unsubstituted or substituted with one or more halogen atoms or $C_1$-$C_{12}$ alkylthio groups; a $C_7$-$C_{20}$ alkylaryl group which is unsubstituted or substituted with one or more halogen atoms; or a $C_1$-$C_{12}$ alkoxy-$C_1$-$C_4$ alkyl group which is unsubstituted or substituted with one or more halogen atoms.

4. The sulfonic acid derivative compound of naphthalimide according to claim 1, wherein $R_1$ is methyl group, ethyl group, trifluoromethyl group, 2,2,2-trifluoroethyl group, nonafluorobutyl group or tosyl group;

$R_2$ is methyl group, ethyl group, propyl group, isopropyl group, butyl group, pentyl group, octyl group or cyclohexyl group; and $R_3$ is methyl group, ethyl group, propyl group, isopropyl group, butyl group, hexyl group, heptyl group, cyclohexyl group, methoxyethyl group ($CH_3$—O—$CH_2CH_2$—) or butoxyethyl group ($CH_3CH_2CH_2CH_2$—O—$CH_2CH_2$—).

5. The sulfonic acid derivative compound of naphthalimide according to claim 1, which is selected from the following compounds:

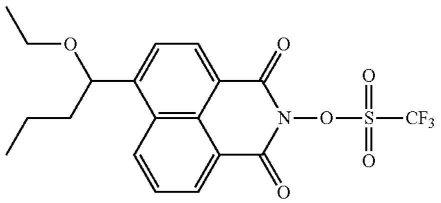

-continued
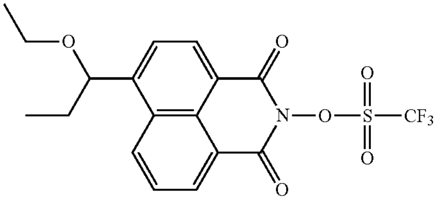
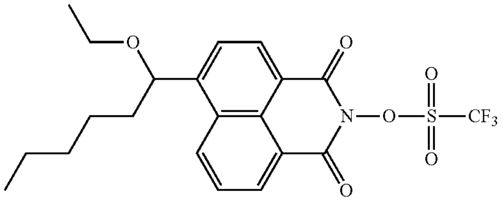
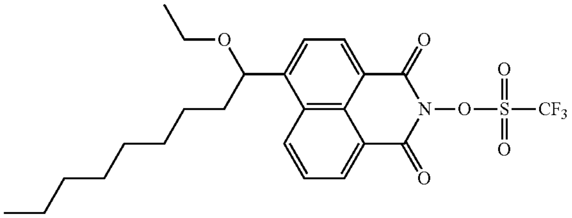
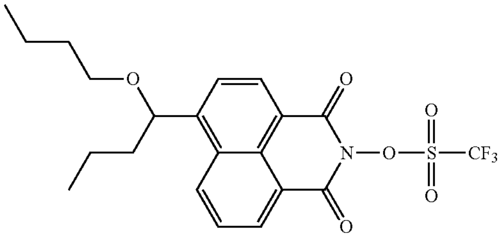
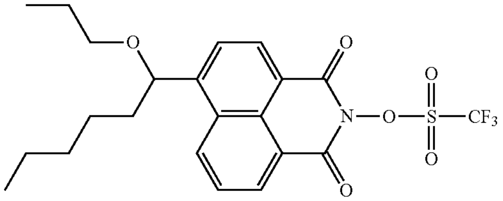
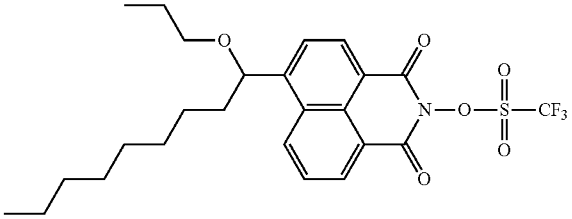
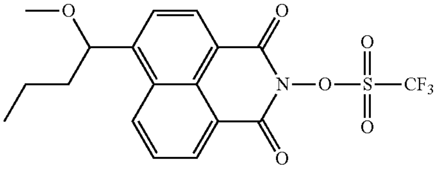
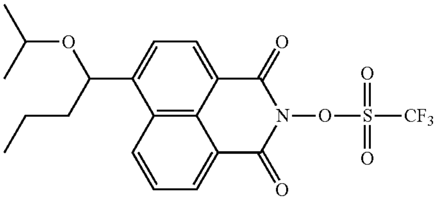
-continued
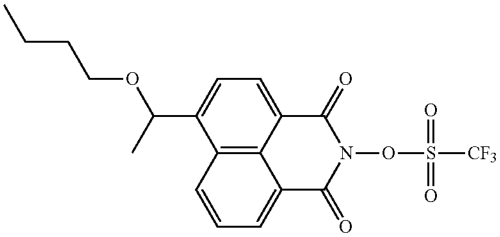
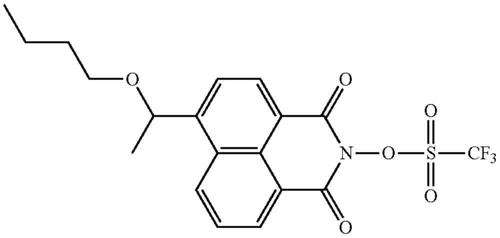
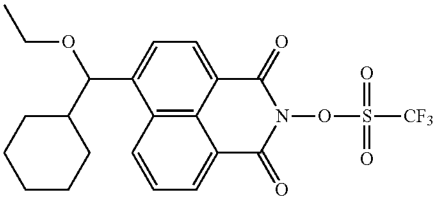
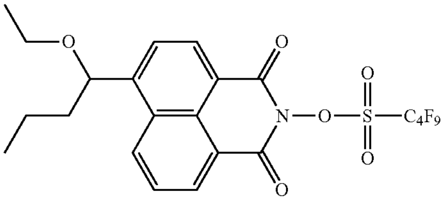
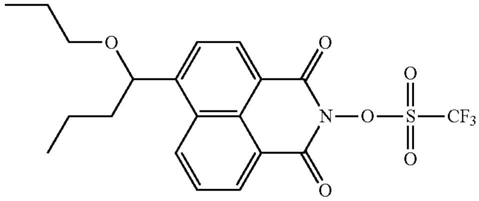
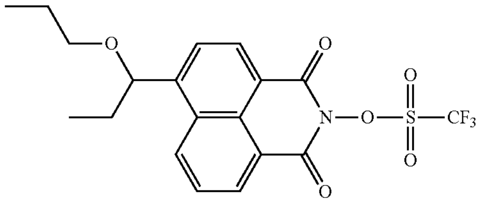
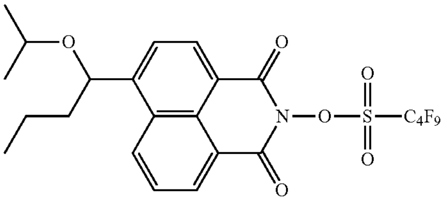

-continued

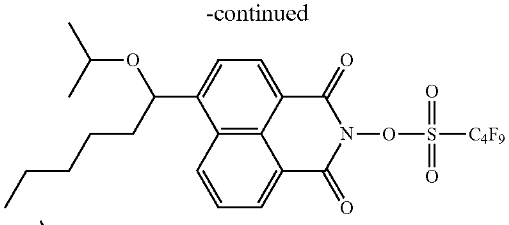

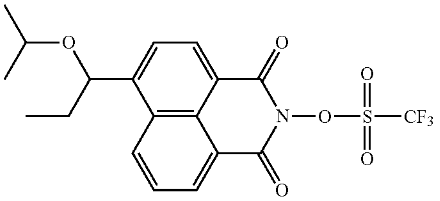

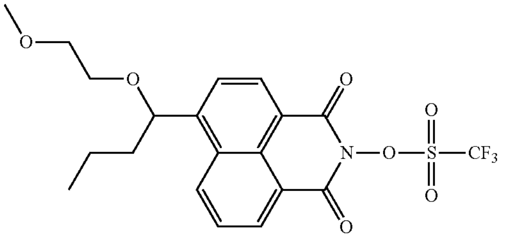

-continued

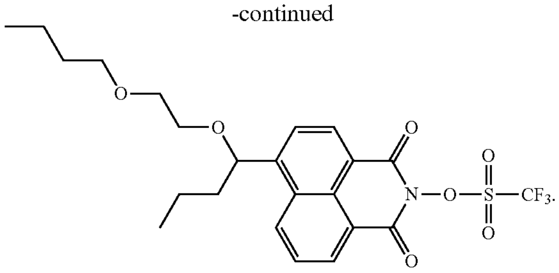

6. A photoacid generator comprising a sulfonic acid derivative compound of naphthalimide according to claim 1.

7. A photoresist composition comprising a sulfonic acid derivative compound of naphthalimide according to claim 1; and a binder resin.

8. A substrate coated with a photoresist composition according to claim 7.

9. A patterned substrate obtained by exposing and developing a coated substrate according to claim 8.

10. A display device comprising a patterned substrate according to claim 9.

11. A semiconductor device comprising a patterned substrate according to claim 9.

* * * * *